United States Patent
Lange et al.

(10) Patent No.: US 8,690,919 B2
(45) Date of Patent: Apr. 8, 2014

(54) SURGICAL SPACER WITH SHAPE CONTROL

(75) Inventors: Eric C Lange, Collierville, TN (US); Hai H Trieu, Cordova, TN (US); Kent M Anderson, Memphis, TN (US); Randall L Allard, Germantown, TN (US); Aurelien Bruneau, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 635 days.

(21) Appl. No.: 12/649,409

(22) Filed: Dec. 30, 2009

(65) Prior Publication Data

US 2010/0114320 A1     May 6, 2010

Related U.S. Application Data (63) Continuation of application No. 11/438,891, filed on May 23, 2006, now abandoned.

(51) Int. Cl.
*A61B 17/70*     (2006.01)
*A61B 17/00*     (2006.01)
*A61F 2/44*     (2006.01)

(52) U.S. Cl.
CPC .......... *A61B 17/7067* (2013.01); *A61B 17/7065* (2013.01); *A61B 2017/00557* (2013.01); *A61F 2002/4495* (2013.01)
USPC ...................................................... 606/249

(58) Field of Classification Search
CPC ........... A61B 17/7067; A61B 17/7065; A61B 2017/00557; A61F 2002/4495
USPC ................................................. 606/248, 249
See application file for complete search history.

(56) References Cited

U.S. PATENT DOCUMENTS

| | | |
|---|---|---|
| 2,077,804 A | 4/1937 | Morrison |
| 2,677,369 A | 5/1954 | Knowles |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

(Continued)

*Primary Examiner* — Ellen C Hammond (57) ABSTRACT

A surgical spacer comprising first and second hollow support members, a flexible container, and a compressible material disposed in the container is disclosed. The first and second support members each have an exterior and an interior cavity. The exteriors of the first and second support members are affixed together and the interior cavities of the first and second support members are connected via a connecting opening. The container is disposed in the interior cavities and extends through the connecting opening. In addition, the container is substantially impermeable to the compressible material. The first and second support members are more rigid than the flexible container. A combination of the first and second support members controls the shape of the flexible container, with the compressible material disposed therein, in response to a compressive load applied to an exterior of the spacer.

20 Claims, 5 Drawing Sheets

(56) References Cited

U.S. PATENT DOCUMENTS

| | | | |
|---|---|---|---|
| 3,648,691 A | 3/1972 | Lumb et al. |
| 3,867,728 A | 2/1975 | Stubstad et al. |
| 4,011,602 A | 3/1977 | Rybicki et al. |
| 4,257,409 A | 3/1981 | Bacal et al. |
| 4,289,123 A | 9/1981 | Dunn |
| 4,401,112 A | 8/1983 | Rezaian |
| 4,553,273 A | 11/1985 | Wu |
| 4,554,914 A | 11/1985 | Kapp et al. |
| 4,573,454 A | 3/1986 | Hoffman |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,657,550 A | 4/1987 | Daher |
| 4,686,970 A | 8/1987 | Dove et al. |
| 4,827,918 A | 5/1989 | Olerud |
| 4,863,476 A | 9/1989 | Shepperd |
| 4,886,405 A | 12/1989 | Blomberg |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,171,280 A | 12/1992 | Baumgartner |
| 5,201,734 A | 4/1993 | Cozad et al. |
| 5,290,312 A | 3/1994 | Kojimoto et al. |
| 5,306,275 A | 4/1994 | Bryan |
| 5,306,310 A | 4/1994 | Siebels |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,415,661 A | 5/1995 | Holmes |
| 5,437,672 A | 8/1995 | Alleyne |
| 5,454,812 A | 10/1995 | Lin |
| 5,458,641 A | 10/1995 | Ramirez Jimenez |
| 5,496,318 A | 3/1996 | Howland et al. |
| 5,518,498 A | 5/1996 | Lindenberg et al. |
| 5,549,679 A | 8/1996 | Kuslich |
| 5,554,191 A | 9/1996 | Lahille et al. |
| 5,562,736 A | 10/1996 | Ray et al. |
| 5,609,634 A | 3/1997 | Voydeville |
| 5,609,635 A | 3/1997 | Michelson |
| 5,628,756 A | 5/1997 | Barker, Jr. et al. |
| 5,645,597 A | 7/1997 | Krapiva |
| 5,645,599 A | 7/1997 | Samani |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,746,762 A | 5/1998 | Bass |
| 5,755,797 A | 5/1998 | Baumgartner |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,066,154 A | 5/2000 | Reiley et al. |
| 6,068,630 A | 5/2000 | Zucherman et al. |
| 6,126,689 A | 10/2000 | Brett |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,451,019 B1 | 9/2002 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,533 B1 | 5/2004 | Lozier |
| 6,733,534 B2 | 5/2004 | Sherman |
| 6,736,818 B2 | 5/2004 | Perren et al. |
| 6,758,863 B2 | 7/2004 | Estes et al. |
| 6,761,720 B1 | 7/2004 | Senegas |
| 6,770,096 B2 | 8/2004 | Bolger et al. |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,958,077 B2 | 10/2005 | Suddaby |
| 6,969,404 B2 | 11/2005 | Ferree |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,377,942 B2 | 5/2008 | Berry |
| 7,442,208 B2 | 10/2008 | Mathieu et al. |
| 7,445,637 B2 | 11/2008 | Taylor |
| 7,582,106 B2 | 9/2009 | Teitelbaum et al. |
| 7,998,174 B2 * | 8/2011 | Malandain et al. ........... 606/249 |
| 2002/0143331 A1 | 10/2002 | Zucherman et al. |
| 2003/0153915 A1 | 8/2003 | Nekozuka et al. |
| 2004/0083002 A1 | 4/2004 | Belef et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |

(56) References Cited

U.S. PATENT DOCUMENTS

| | | |
|---|---|---|
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241613 A1 | 10/2006 | Brueneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0293662 A1 | 12/2006 | Boyer, II et al. |
| 2006/0293663 A1 | 12/2006 | Walkenhorst et al. |
| 2007/0043362 A1 | 2/2007 | Malandain et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0191838 A1 | 8/2007 | Bruneau et al. |
| 2007/0198091 A1 | 8/2007 | Boyer et al. |
| 2007/0203493 A1* | 8/2007 | Zucherman et al. ............ 606/61 |
| 2007/0225807 A1 | 9/2007 | Phan et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1 | 11/2007 | Bruneau et al. |
| 2007/0276369 A1 | 11/2007 | Allard et al. |
| 2007/0276493 A1 | 11/2007 | Malandain et al. |
| 2007/0282443 A1 | 12/2007 | Globerman et al. |
| 2008/0021457 A1 | 1/2008 | Anderson et al. |
| 2008/0058934 A1 | 3/2008 | Malandain et al. |
| 2008/0161818 A1 | 7/2008 | Kloss et al. |
| 2008/0221685 A9 | 9/2008 | Altarac et al. |
| 2008/0262617 A1 | 10/2008 | Froehlich et al. |
| 2009/0270918 A1 | 10/2009 | Attia et al. |

FOREIGN PATENT DOCUMENTS

| | | |
|---|---|---|
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 99/26562 | 6/1999 |
| WO | WO 99/59669 | 11/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | WO 2005/002474 A1 | 1/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

(56) References Cited

OTHER PUBLICATIONS

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologic rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," Spine, 1991, pp. S298-S301, vol. 16, No. 6, Supplement.

Zucherman et al., "Clinical Efficacy of Spinal Instrumentation in Lumbar Degenerative Disc Disease," Spine, Jul. 1992, pp. 834-837, vol. 17, No. 7.

\* cited by examiner

SURGICAL SPACER WITH SHAPE CONTROL

CROSS-REFERENCE TO RELATED APPLICATIONS/PATENTS

This application is a continuation of prior application Ser. No. 11/438,891, filed May 23, 2006, now abandoned, the entirety of which is incorporated herein by reference.

In addition, this application contains subject matter which is related to the subject matter of the following applications. Each of the below listed applications is hereby incorporated herein by reference in its entirety: "Surgical Spacer," by Anderson (U.S. patent application Ser. No. 11/438,940); and "Systems and Methods for Adjusting Properties of a Spinal Implant," by Trieu et al. (U.S. patent application Ser. No. 11/439,006).

TECHNICAL FIELD

The present invention generally relates to surgical spacers for spacing adjacent body parts. More particularly, the present invention relates to surgical spacers having a flexible container for containing a material that is compressible during end use, the container being substantially impermeable to the material, and a structure for controlling at least part of a shape of the container when containing the material.

BACKGROUND OF THE INVENTION

The human spine is a biomechanical structure with thirty-three vertebral members, and is responsible for protecting the spinal cord, nerve roots and internal organs of the thorax and abdomen. The spine also provides structural support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, the natural aging process, or the result of a degenerative disease or condition.

Procedures to address back problems sometimes require correcting the distance between spinous processes by inserting a device (e.g., a spacer) therebetween. The spacer, which is carefully positioned and aligned within the area occupied by the interspinous ligament, after removal thereof, is sized to position the spinous processes in a manner to return proper spacing thereof.

Dynamic interspinous spacers are currently used to treat patients with a variety of indications. Essentially, these patients present a need for distraction of the posterior elements (e.g., the spinal processes) using a mechanical device. Current clinical indications for the device, as described at SAS (Spine Arthroplasty Society) Summit 2005 by Guizzardi et al., include stenosis, disc herniation, facet arthropathy, degenerative disc disease and adjacent segment degeneration.

Marketed interspinous devices include rigid and flexible spacers made from PEEK, titanium or silicone. Clinical success with these devices has been extremely positive so far as an early stage treatment option, avoiding or delaying the need for lumbar spinal fusion. However, all devices require an open technique to be implanted, and many require destroying important anatomical stabilizers, such as the supraspinous ligament.

Current devices for spacing adjacent interspinous processes are preformed, and are not customizable for different sizes and dimensions of the anatomy of an interspinous area of an actual patient. Instead, preformed devices of an approximately correct size are inserted into the interspinous area of the patient. Further, the stiffness or flexibility of the devices must be determined prior to the devices being inserted into the interspinous area.

Thus, a need exists for improvements to surgical spacers, such as those for spacing adjacent interspinous processes.

SUMMARY OF THE INVENTION

Briefly, the present invention satisfies the need for improvements to surgical spacers by providing shape control. A flexible container is provided that is fillable in situ to a desired amount, with a structure for at least part of the container providing shape control thereto. An optional conduit coupled to the container allows for filling of the container, for example, by injecting a material into the container.

The present invention provides in a first aspect, a surgical spacer. The surgical spacer comprises a flexible container for containing a material that is compressible during end use, wherein the container is substantially impermeable to the material. The surgical spacer further comprises a structure for at least part of the container when containing the material, wherein the structure controls at least part of a shape of the surgical spacer.

The present invention provides in a second aspect, an interspinous spacer. The interspinous spacer comprises a flexible container for containing an injectable material that is compressible during end use, wherein the container is substantially impermeable to the injectable material. The interspinous spacer further comprises a conduit coupled to the container for accepting the injectable material, and a structure for at least part of the container when containing the material, wherein the structure has a shape during end use to fit between adjacent spinous processes.

The present invention provides in a third aspect, a method of controlling at least part of a shape of a surgical spacer. The surgical spacer comprises a flexible container for containing a material that is compressible during end use, wherein the container is substantially impermeable to the material. The surgical spacer further comprises a structure for at least part of the container when containing the material. The method comprises creating the structure with at least one material for controlling at least part of a shape of the surgical spacer during end use.

The present invention provides in a fourth aspect, a method of spacing adjacent spinous processes. The method comprises providing an interspinous spacer, the interspinous spacer comprising a flexible container for containing an injectable material that is compressible during end use, wherein the container is substantially impermeable to the injectable material. The interspinous spacer further comprises a conduit coupled to the container for accepting the injectable material, and a structure for at least part of the container when containing the material, wherein the structure has a shape during end use to fit between adjacent spinous processes. The method further comprises implanting the interspinous spacer between adjacent spinous processes, and injecting the injectable material into the container through the conduit such that the shape is achieved.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION OF THE INVENTION

A surgical spacer of the present invention can be formed in situ during a procedure. The spacer includes the following basic aspects: a flexible container, and a structure for at least part of the container that controls at least part of the shape of the surgical spacer. The flexible container can be filled or injected through an optional conduit after placement. Further, the structure may be folded or otherwise reduced in size prior to use in some aspects. Together with an unfilled container, in some aspects, the spacer can create a smaller footprint during implantation. Once filled, the structure provides support and containment for the container, as well as providing shape control for at least part of the spacer.

Figure 1:
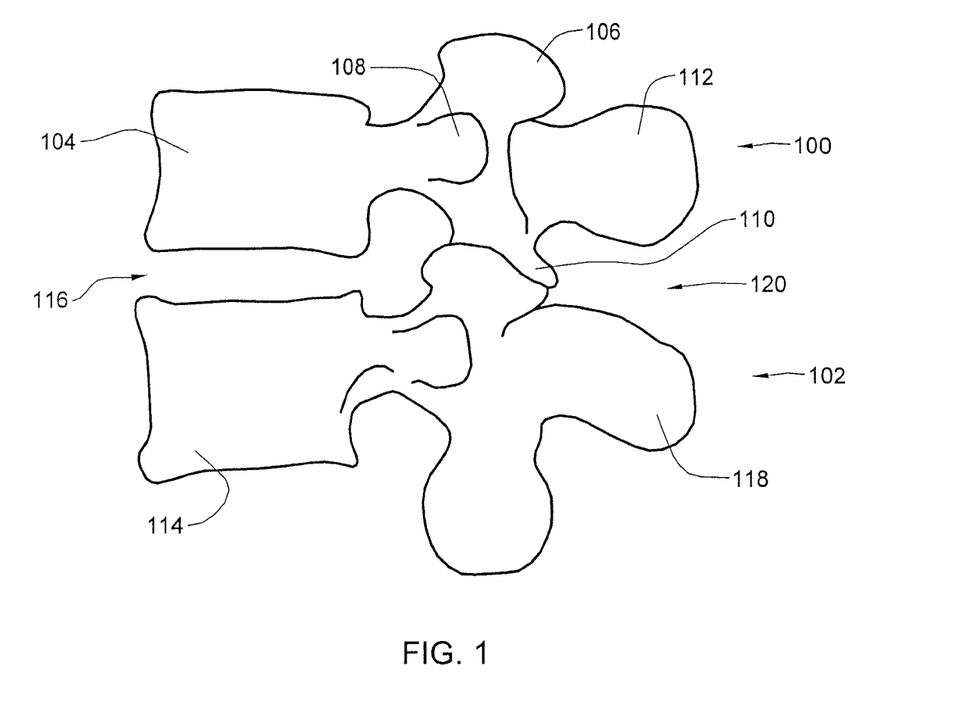
FIG. 1 depicts adjacent vertebrae of the lumber region of a human spinal column.

FIG. 1 depicts adjacent vertebrae 100, 102 of the lumbar region of a human spinal column. As known in the art, each vertebrae comprises a vertebral body (e.g., vertebral body 104), a superior articular process (e.g., superior articular process 106), a transverse process (e.g., transverse process 108), an inferior articular process (e.g., inferior articular process 110), and a spinous process (e.g., spinous process 112). In addition, between vertebral bodies 104 and 114 is a space 116 normally occupied by an intervertebral disc (see FIG. 2), and between spinous processes 112 and 118 is a space 120 normally occupied by an interspinous ligament (see FIG. 2).

Figure 2:
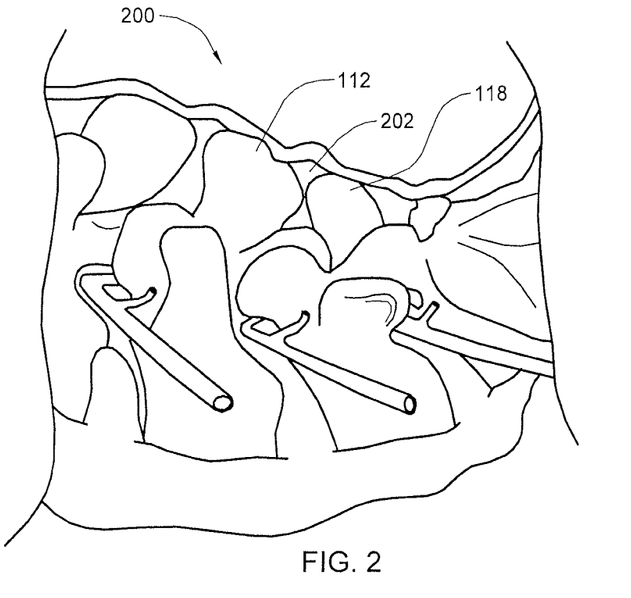
FIG. 2 depicts a more detailed view of a portion of a human spinal column including the vertebrae of FIG. 1.

FIG. 2 depicts the vertebrae of FIG. 1 within an area 200 of the lumbar region of a human spine. As shown in FIG. 2, spinous processes 112 and 118 are touching and pinching interspinous ligament 202, calling for spacing of the spinous processes.

Figure 3:
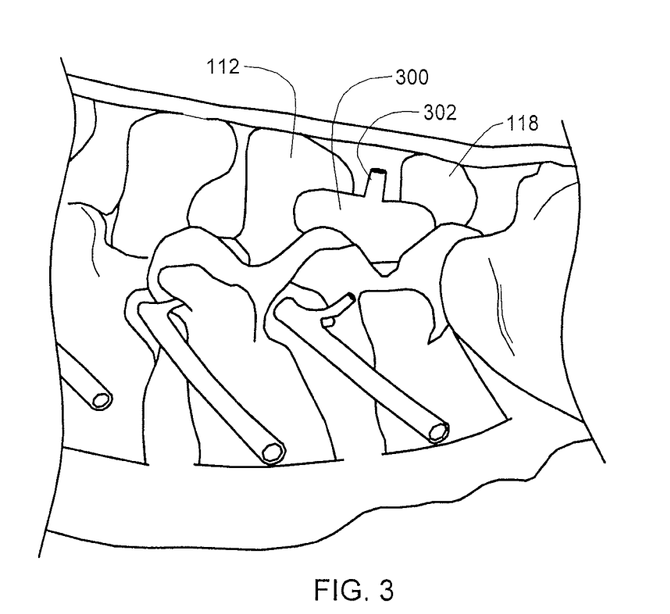
FIG. 3 depicts the spinal column portion of FIG. 2 after implantation and filling of one example of an interspinous spacer in accordance with an aspect of the present invention.

FIG. 3 depicts spinous processes 112 and 118 after spacing with an interspinous spacer 300 in accordance with one aspect of the present invention. As shown in FIG. 3, interspinous ligament 202 has been removed in a conventional manner prior to insertion of spacer 300. Although shown in its filled state, in this example, spacer 300 is implanted in its unexpanded state, as described more fully below. The spacer is filled with a material described below through a conduit 302 after implantation. For example, the material may be injected into the spacer through the conduit (e.g., a one-way valve). Prior to implantation and filling, measurement of the space between the interspinous processes and determination of the spacer size and desired amount of filling can be performed. Conventional methods can be used, such as, for example, the use of templates, trials, distractors, scissor-jacks or balloon sizers.

Figure 4:
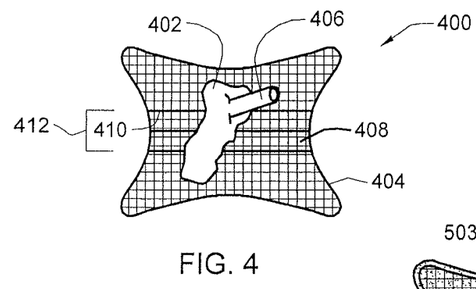
FIG. 4 is a partial cut-away view of one example of an unfilled surgical spacer with the container in the structure, in accordance with an aspect of the present invention.

FIG. 4 depicts a partially cut-away view of one example of a spacer 400, in accordance with one aspect of the present invention. As shown in FIG. 4, the spacer comprises an unfilled container 402 inside a structure 404. Preferably, the container is in an evacuated state during implantation and prior to being filled. Where a valve (e.g., a one-way valve) is coupled to the container, the container is preferably evacuated prior to or during the process of coupling the valve thereto. In the present example, the structure is outside the container. However, as will be described in more detail below, the container can be outside the structure, or the container and structure can be integrated. In addition, although the structure is shown to be roughly H-shaped to fit between adjacent spinous processes, the structure can have any shape necessary for the particular surgical application. For example, the structure could instead have a roughly cylindrical shape to replace an intervertebral disc. As another example, the structure could be spherically or elliptically shaped to replace part of the intervertebral disc, for example, the nucleus pulpous, leaving the rest of the disc intact. Further, although the structure is shown enveloping the container, the structure could be for only a portion of the container, depending on the particular application. For example, it may be desired to prevent bulging of the container only in a particular area. Coupled to the container is an optional conduit 406 for accepting a material that is compressible during end use. The structure provides support for and containment of the container when filled.

The container is flexible and substantially impermeable to the material it will be filled with. However, depending on the application, the container may be permeable to other materials, for example, it may be air and/or water permeable. In the present example, the container takes the form of a bag or balloon, but can take other forms, so long as flexible and substantially impermeable to the material it will be filled with. Thus, the container must be substantially impermeable to the filling material, for example, in a liquid state during filling and prior to curing. Examples of container materials include silicone, rubber, polyurethane, polyethylene terephthalate (PET), polyolefin, polycarbonate urethane, and silicone copolymers.

Conduit 406 accepts the material being used to fill the container. Preferably, the conduit comprises a one-way valve, however, a two-way valve is also contemplated, as another example. The conduit can comprise any material suitable for implanting, for example, various plastics. Also preferably, the conduit is constructed to be used with a delivery system for filling the container, such as, for example, a pressurized syringe-type delivery system. However, the delivery system itself forms no part of the present invention. As noted above, the conduit is optional. Other examples of how to fill the container comprise the use of a self-sealing material for the container, or leaving an opening in the container that is closed (e.g., sewn shut) intraoperatively after filling. Using a curable material to fill the container may also serve to self-seal the container.

In use, the container is filled with a material that is compressible during end use. The compressibility characteristic ensures that the material exhibits viscoelastic behavior and that, along with the structure, the spacer can accept compressive loads. Of course, the degree of compressibility will depend on the particular application for the surgical spacer. For example, if a spacer according to the present invention is used between adjacent spinous processes, the spacer would need to accept compressive loads typically experienced in the posterior region of the spine, for example, up to about 80 shore A. In other words, the spacer is preferably capable of resisting compressive motion (or loads) with a stiffness of about 40 to about 240 N/mm (newtons per millimeter). The material is preferably injectable, and may be compressible immediately or after a time, for example, after curing. For purposes of the invention, the compressibility characteristic is necessary during end use, i.e., after implantation. Materials that could be used include, for example, a plurality of beads (e.g., polymer beads) that in the aggregate are compressible, or materials that change state from exhibiting fluid properties to exhibiting properties of a solid or semi-solid. Examples of such state-changing materials include two-part curing polymers and adhesive, for example, platinum-catalyzed silicone, epoxy, polyurethane, etc.

As noted above, the structure provides support for and containment of the container when filled, as well as at least partial shape control of the spacer. The structure comprises, for example, a structural mesh comprising a plurality of fibers and/or wires 408. Within the structural mesh are shape-control fibers and/or wires 410. In one example, shape control is provided by wires of a shape-memory alloy (e.g., Nitinol). The shape-memory alloy wire(s) can be coupled to the structural mesh (inside or outside), or weaved into the mesh (i.e., integrated). Coupling can be achieved, for example, by stitching, twisting, or closing the wire on itself. Alternatively, shape control can be provided by other wires or fibers that do not "give" in a particular direction, for example, metal or metal alloys (e.g., tantalum, titanium or steel, and non-metals, for example, carbon fiber, PET, polyethylene, polypropalene, etc.). The shape-memory alloy can be passive (e.g., super-elastic) or active (e.g., body-temperature activated). The use of metal, metal alloy or barium coated wires or fibers can also improve radiopacity for imaging. The remainder of the structure can take the form of, for example, a fabric jacket, as shown in FIG. 4. Although the shape-memory alloy wires make up only a portion of the structural mesh of FIG. 4, it will be understood that there could be more such wires, up to and including comprising the entirety of the mesh. The fabric jacket in this example contains and helps protect the container from bulging and damage from forces external to the container, while the shape-memory alloy provides shape control of the spacer in a center region 412. The fibers of the jacket comprise, for example, PET fabric, polypropylene fabric, polyethylene fabric and/or steel, titanium or other metal wire. Depending on the application, the structure may be permeable to a desired degree. For example, if bone or tissue growth is desired to attach to the structure, permeability to the tissue or bone of interest would be appropriate. As another example, permeability of the structure may be desired to allow the material used to fill the container to evacuate air or water, for example, from the container, in order to prevent bubbles from forming inside. Where a mesh is used, for example, the degree of permeability desired can be achieved by loosening or tightening the weave.

Although the structure is shown in a roughly H-shape in the example of FIG. 4, it will be understood that in practice, the structure can be made to be folded, unexpanded, or otherwise compacted. This is particularly true where, for example, the structure comprises a fabric or other easily folded material. A folded or unexpanded state facilitates implantation, allowing for a smaller surgical opening, and unfolding or expansion in situ upon filling of the container. Further, the structure can have a different final shape, depending on the shape-control material used. For example, the shape-memory wires in FIG. 4 may be in their inactive state, whereupon activation by body temperature causes contraction thereof, making the spacer of FIG. 4 "thinner" than shown in the center region.

Figure 7:
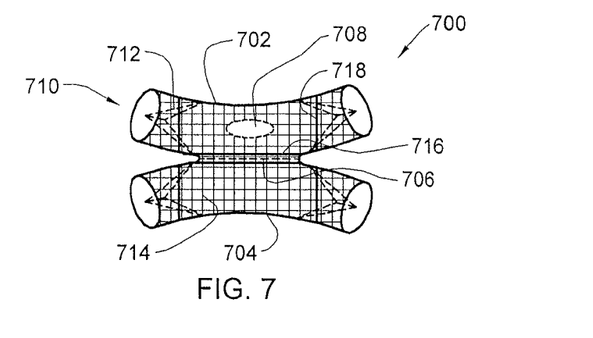
FIG. 7 depicts one example of the construction of a structure for use with one example of a surgical spacer, in accordance with another aspect of the present invention.

One example of the construction of a structural mesh 700 for use as one example of a structure of the present invention will now be described with reference to FIG. 7. Two roughly cylindrical members 702 and 704 are sewn together around a periphery 706 of an opening along a side (not shown) in each. Each member in this example comprises a fabric mesh (e.g., fabric mesh 714) similar in composition to the fabric jacket of FIG. 4. Interwoven with the fabric are a plurality of shape-memory alloy wires both horizontally (e.g., wire 716) and vertically (e.g., wire 718). An opening 708 is created in one of the members for accepting the container, for example, by laser cut. In one example, a conduit described above would poke through opening 708. The ends of the cylindrical members (e.g., end 710) are then trimmed and sewn shut, as shown in broken lines (e.g., lines 712) in FIG. 7.

Figure 5:
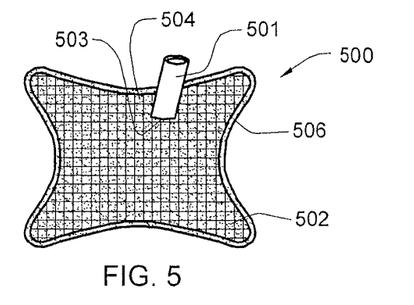
FIG. 5 depicts an example of a surgical spacer with integrated container and structure, in accordance with an aspect of the present invention.

FIG. 5 depicts an outer view of another example of a surgical spacer 500 in accordance with an aspect of the present invention. A container conduit 501 is shown pointing outward from an opening 503. As shown, the structure 502 delimits the final shape of the spacer, in this example, a rough H-shape. The structure comprises a mesh 504 of shape-memory alloy wire, that is soaked through with a dispersion polymer 506 (e.g., silicone). The dispersion polymer (after curing) acts as the container and is shown filled in FIG. 5. This is one example of the container and the structure being integral. Although the mesh of FIG. 5 is described as being all shape-memory alloy wire, it will be understood that, like FIG. 4, the shape-memory alloy could only form a part of the structure.

Figure 6:
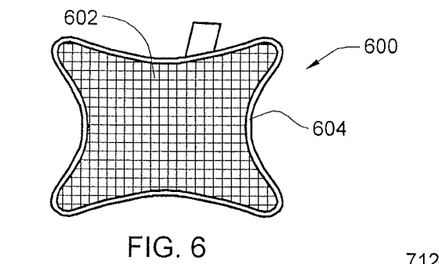
FIG. 6 is a cross-sectional view of one example of a surgical spacer with external container, in accordance with an aspect of the present invention.

FIG. 6 is a cross-sectional view of another example of a surgical spacer 600 in accordance with the present invention. Surgical spacer 600 is similar to the spacer of FIG. 5, except that instead of being soaked in a dispersion polymer, a structural mesh 602 of a shape-memory alloy wire is coated with a dispersion polymer (e.g., silicone) 604 or other curable liquid appropriate for the container material, creating an outer container. The coating can be done in a conventional manner, for example, by dip molding on the outside of the mesh.

Figure 8:
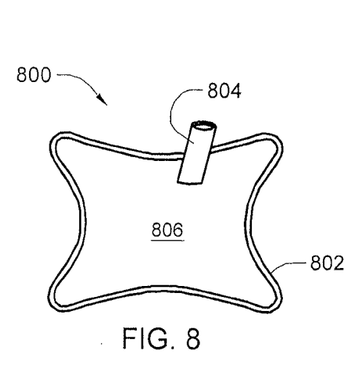
FIG. 8 depicts another example of a surgical spacer with integrated container and structure, in accordance with another aspect of the present invention.

FIG. 8 depicts another example of a surgical spacer 800 with an integrated container and structure, in accordance with another aspect of the present invention. The container and structure in the example of FIG. 8 both comprise a single layer 802 of rubber that is thick enough for a given application to perform the functions of both the container and structure (including shape control). Such a rubber shell would be able to return to its original shape when unconstrained. In addition, spacer 800 preferably includes a conduit 804 (preferably, a one-way valve) for filling internal space 806. The material can be any of the filling materials described above, for example, silicone. Where the spacer is used, for example, to space adjacent spinous processes, the thickness of layer 802 is preferably in the range of about 0.2 mm to about 2.5 mm. A layer of rubber of that thickness will contain the material chosen, and, when filled, will sufficiently maintain the shape of the spacer for the intended use.

In an alternate aspect, the rubber shell of FIG. 8 can be augmented with internal, external, or integrated features to further control shape. Examples of such features include thread, wires (e.g., metal, including shape-memory alloys), cables, tethers, rings or a mesh.

Figures 9, 10:
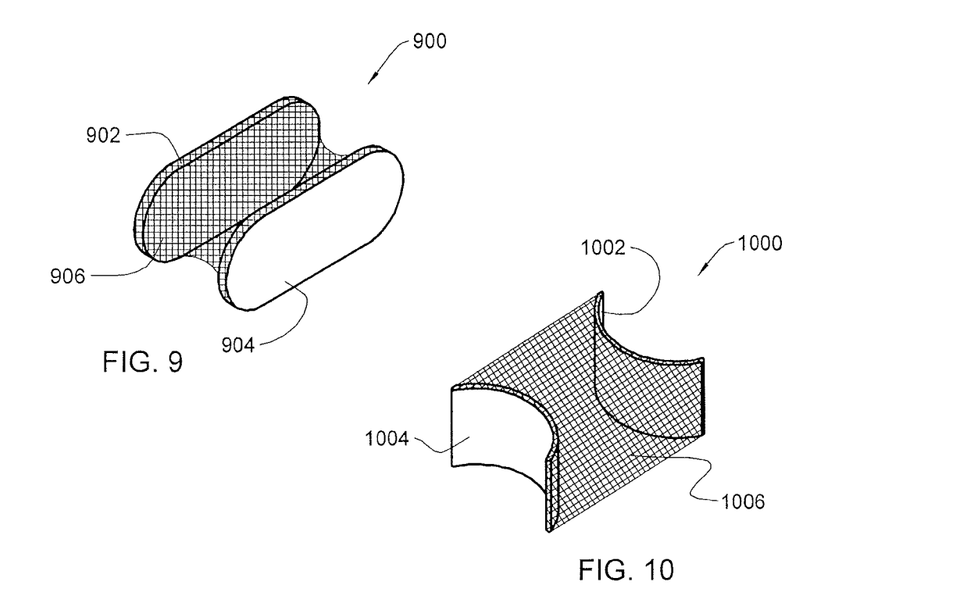
FIG. 9 depicts one example of a structure for a surgical spacer including at least one substantially inflexible shaped member, in accordance with another aspect of the present invention.
FIG. 10 depicts another example of a structure for a surgical spacer including at least one substantially inflexible shaped member, in accordance with another aspect of the present invention.

FIG. 9 depicts one example of a structure for a surgical spacer including at least one substantially inflexible shaped member, in accordance with another aspect of the present invention. The substantially inflexible member(s) are used to achieve at least part of a preformed shape for a given application. Structure 900 comprises blades 902 and 904 that are substantially inflexible and are substantially straight. In one example, the blades comprise metal, such as, for example, a nickel-titanium alloy. The blades provide a specific shape for at least part of the surgical spacer. Coupling the blades is, for example, a structural mesh 906. The structure can be paired with any of the types of containers described herein. In addition, the structural mesh can take any of the forms described herein. For example, the structural mesh could take the form of a PET fabric mesh, with or without other shape-enhancing elements (e.g., shape-memory alloy fabric or wire). In one example, the mesh covers the blades. In another example, the mesh is coupled at a periphery of the blades.

Figure 12:
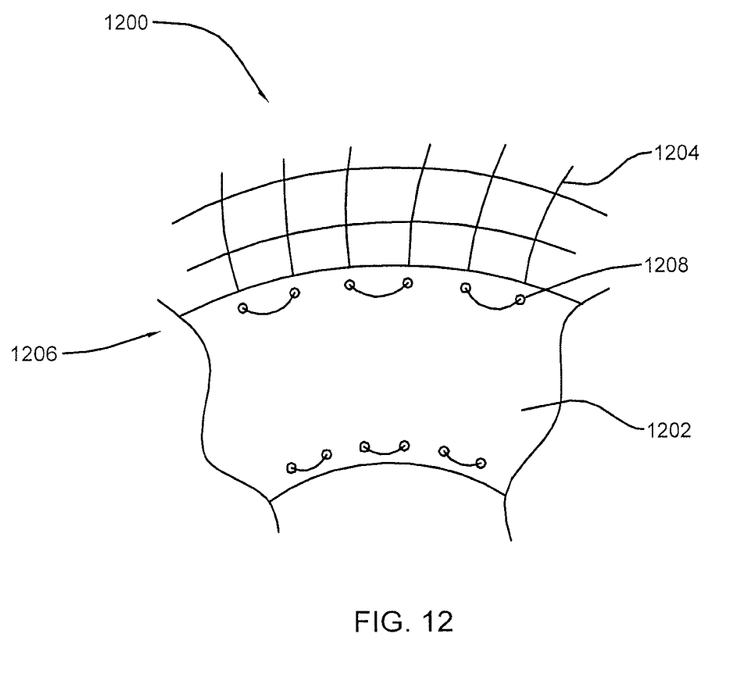
FIG. 12 depicts a portion of a surgical spacer with a structural mesh coupled at least one least one substantially inflexible shaped member, in accordance with another aspect of the present invention.

As shown in the example of FIG. 12, a portion of a surgical spacer 1200 comprises a blade 1202 and structural mesh 1204. At the periphery 1206 of the blade, the mesh is coupled to the blade by stitching through a plurality of holes (e.g., hole 1208).

Similarly, FIG. 10 depicts another example of a structure 1000 including at least one substantially inflexible shaped member. In this example, there are two substantially inflexible shaped members 1002 and 1004, each being roughly U-shaped. In one example, the U-shaped members comprise metal blades, such as, for example, nickel-titanium alloy blades. Coupling the blades is, for example, a structural mesh 1006 similar to that described above with respect to FIG. 9. In addition, as also noted above with respect to FIG. 9, the structure of FIG. 10 can be paired with any of the containers described herein.

Figure 11:
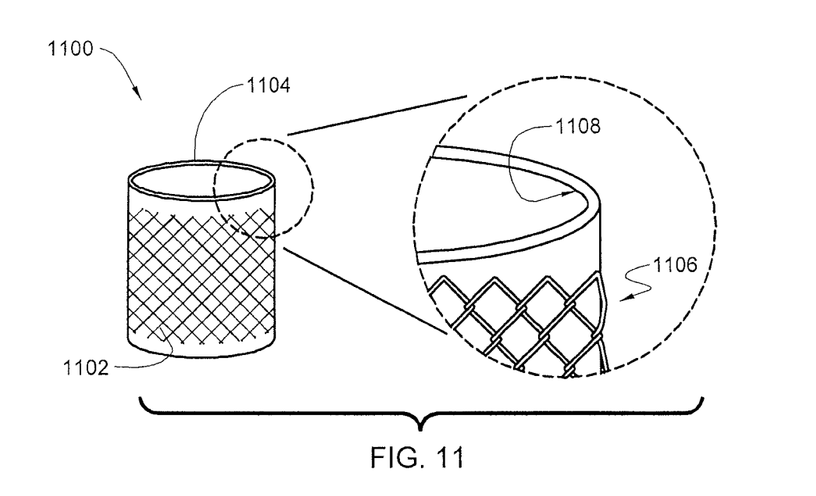
FIG. 11 depicts still another example of a structure for a surgical spacer including a supra-structure, in accordance with another aspect of the present invention.

FIG. 11 depicts still another example of a structure 1100 for a surgical spacer, in accordance with another aspect of the present invention. In this example, the structure comprises a supra-structure 1102 coupled to a main structure 1104. The main structure need not provide shape control, since that is provided by the supra-structure, however, it could also provide shape control. For example, the main structure could provide shape control in one or more directions, while the supra-structure provides shape control in one or more other directions. Of course, the supra-structure could provide shape control uniformly, e.g., if added to all surfaces. In one example, the main structure comprises a fabric mesh (e.g., PET fabric) with or without added shape memory control fibers or wires. In one example, shown inset in FIG. 11, supra-structure 1102 comprises a plurality of interlocking links 1106, the links comprising, for example, a shape-memory alloy. The links could provide resistance to expansion in one or more directions or uniformly, and/or could allow pliability, permitting deformation in one or more directions. The supra-structure can be loosely or rigidly coupled to the main structure, for example, via loops, hooks, stitches or frictional mechanisms. Of course, the supra-structure could instead be coupled to an inside 1108 of the main structure in another example. As with other embodiments herein, the shape-memory alloy can be passive (e.g., superelastic) or active (e.g., body-temperature activated).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A surgical spacer comprising:
   a structure having an outer surface, first and second support members and an interior cavity, wherein the structure includes a plurality of outer edges each being concave in shape;
   a flexible container disposed in the interior cavity of the structure;
   a compressible material disposed within the container; the container substantially impermeable to the material;
   the first and second support members being more rigid than the flexible container such that the first and second support members provide shape control of the flexible container at a center region by contracting the center region;
   a combination of the first and second support members controlling a shape of the flexible container, with the compressible material disposed therein, in response to a compressive load applied to an exterior of the spacer; wherein
   the structure comprises a woven mesh exterior configured to provide a variable degree of permeability that is controlled by loosening or tightening of a weave in the woven mesh exterior.

2. The spacer of claim 1 wherein the first and second support members are elongate in generally parallel directions.

3. The spacer of claim 1 wherein the woven mesh exterior comprises a plurality of shape-memory alloy wires.

4. The spacer of claim 3 wherein the shape-memory alloy wires are interwoven in two directions.

5. The spacer of claim 3 wherein the shape-memory alloy wires are initially in an inactive state.

6. The spacer of claim 5 wherein the shape-memory alloy wires are activated by body temperature.

7. The spacer of claim 6 wherein when the shape-memory alloy wires are activated, the wires contract the center region.

8. The spacer of claim 1 further comprising a conduit extending through an exterior of the first support member and fluidically coupled to the flexible container for delivery of the compressible material thereto.

9. The spacer of claim 8 wherein the conduit includes a one-way valve.

10. The spacer of claim 8 wherein the conduit includes a two-way valve.

11. The spacer of claim 1 wherein the first support member comprises a first end portion, a second end portion, and an intermediate portion; wherein the second support member comprises a first end portion, a second end portion, and an intermediate portion; wherein the connecting opening connects the intermediate portions of the first and second support members; wherein the first and second end portions of the first and second support members narrow in a direction away from the respective intermediate portions.

12. The spacer of claim 1 wherein the first and second support members are generally cylindrical in shape.

13. The spacer of claim 1 wherein the compressible material is selected from the group consisting of platinum-catalyzed silicone, epoxy, and polyurethane.

14. The spacer of claim 1 wherein the spacer is configured to be folded for implantation into a human body.

15. The spacer of claim 14 wherein the spacer is configured to be unfolded upon implantation into the body.

16. The spacer of claim 1 wherein the spacer is configured to be implanted into a human body in an unexpanded shape.

17. The spacer of claim 1 wherein contracting the center region forms an H-shaped spacer.

18. The spacer of claim 1 wherein the flexible container is disposed partially within structure.

19. The spacer of claim 1 wherein the flexible container is disposed outside structure.

20. The spacer of claim 1 wherein the woven mesh exterior partially comprises a plurality of shape-memory alloy wires, wherein the shape-memory wires are coupled to the woven mesh exterior by stitching, twisting, or closing the plurality of shape-memory wires on itself.

\* \* \* \* \*